United States Patent
Mine et al.

[11] Patent Number: 6,103,517
[45] Date of Patent: Aug. 15, 2000

[54] PROCESS FOR THE PRODUCTION OF AN OPTICALLY ACTIVE ALCOHOL AND A NOVEL OPTICALLY ACTIVE ALCOHOL

[75] Inventors: Takakiyo Mine; Hiroshi Mineta; Tomoyuki Yui; Masahiro Johno, all of Tsukuba, Japan

[73] Assignee: Mitsubishi Gas Chemical Company, Tokyo, Japan

[21] Appl. No.: 09/260,482

[22] Filed: Mar. 2, 1999

Related U.S. Application Data

[63] Continuation-in-part of application No. 08/923,405, Sep. 4, 1997, abandoned.

[30]    Foreign Application Priority Data

Sep. 11, 1996  [JP]  Japan ................................ 2-240519
Sep. 26, 1996  [JP]  Japan ................................ 8-284749

[51] Int. Cl.$^7$ .................................................. C12P 41/00
[52] U.S. Cl. ........................... 435/280; 568/579; 568/671
[58] Field of Search .................... 568/671, 579; 435/280

[56]    References Cited

U.S. PATENT DOCUMENTS

| | | | |
|---|---|---|---|
| 4,963,492 | 10/1990 | Keller et al. ............................ | 435/280 |
| 5,223,633 | 6/1993 | Hoppe et al. . | |
| 5,534,436 | 7/1996 | Wasserthal et al. .................... | 435/280 |

FOREIGN PATENT DOCUMENTS

| | | |
|---|---|---|
| 643154 | 1/1989 | Japan . |
| 1213390 | 8/1989 | Japan . |
| 1316339 | 12/1989 | Japan . |
| 1316367 | 12/1989 | Japan . |
| 1316372 | 12/1989 | Japan . |
| 228128 | 1/1990 | Japan . |
| 2225434 | 9/1990 | Japan . |
| 2229128 | 9/1990 | Japan . |
| 2282340 | 11/1990 | Japan . |
| 1565486 | 3/1993 | Japan . |

OTHER PUBLICATIONS

Bianchi et al, J.Org. Chem, vol. 52, pp. 5531–5534, 1988.
Klempier et al, Synthesis, pp. 933–934, 1989.
Yamaguchi et al., "Kagaku" (Chemistry) 42(11), 757 (1987).
Johno, et al., Journal of Organic Synthesis Chem. Soc., 47(6), 568 (1989) Ab.
Lin Katazume et al., J. Org. 52, 3211 (1987).
Kirchner et al., J. Am. Chem. Soc. 1985, 107, 7072–7076.
Novak et al., JACS, 89:1, 73(1967).
Keinan et al., Biocatalysis, 3, 57 (1990).
Chandani et al., Japanese J. of App. Phy. vol. 27, No. 5, L729–L732, May 1988.
Chandani et al., Japanese J. of App. Phy., vol. 28, No. 7, L1261–L1262, 1989.
Chandani et al., Japanese J. of App. Phy. vol. 28, No. 7,L1265–L1268, Jul. 1989.
Johno et al., Japanese J. of App. Phy., vol. 28, No. 1, L119–L120, Jul. 1989.
Johno et al., Japanese J. of App. Phy., vol. 29, No. 1, L111–L114, Jan. 1990.
Higawara et al., "Liquid Crystals", vol. 6, No. 2, 167–174 (1989).

*Primary Examiner*—Shailendra Kumar

[57]    ABSTRACT

A process for the production of R-configuration or S-configuration optically active alcohol having the formula (1), $$CH_3C*H(OH)(CH_2)_m OC_n H_{2n+1} \qquad (1)$$

wherein m is an integer of 3 to 5, n is an integer of 1 to 3, and C* is an asymmetric carbon,
and the formula (2), which comprises carrying out the optical resolution of the racemic alcohol, $$CH_3CH(OH)(CH_2)_m OC_n H_{2n+1} \qquad (2)$$

wherein m is an integer of 3 to 5 and n is an integer of 1 to 3,
into an R-configuration compound and S-configuration compound by the asymmetric trans-esterification thereof is provided in the presence of vinyl propionate as an esterifying agent and a lipase as a catalyst.

5 Claims, No Drawings

PROCESS FOR THE PRODUCTION OF AN OPTICALLY ACTIVE ALCOHOL AND A NOVEL OPTICALLY ACTIVE ALCOHOL

CROSS-REFERENCE TO RELATED APPLICATION

This application is a continuation-in-part of application U.S. Ser. No. 08/923,405 filed Sep. 4, 1997, now abandoned, which is incorporated herein in its entirety by reference thereto.

FIELD OF THE INVENTION

The present invention relates to a process for the production of an optically active alcohol and a novel optically active alcohol. More specifically, it relates to a process for the production of an optically active alcohol by using a specific esterifying agent and a lipase, and a novel optically active secondary alcohol having an asymmetric carbon containing a methyl group thereon and having an alkoxy group as terminal group.

PRIOR ART

Optically active substances have been used in the fields of medicaments and agricultural chemicals, while they are recently attracting attention as functional materials such as ferroelectric liquid crystal compounds and organic non-linear materials.

For example, in the field of organic non-linear materials, molecules of organic materials preferably have an asymmetric center for producing a secondary non-linear optical effect (e.g., Yamaguchi, Nakano and Fueno, "Kagaku" (Chemistry) 42 (11), 757 (1987)). In the field of ferroelectric liquid crystal compounds, liquid crystal molecules are indispensably optically active compounds for exhibition of ferroelectricity by the liquid crystal (e.g., Johno, Fukuda, Journal of Organic Synthesis Chemistry Society, 47 (6), 568 (1989)).

In recent years, further, anti-ferroelectric liquid crystal compounds are attracting considerable attention, but molecules of the anti-ferroelectric liquid crystal compounds are required to be optically active like ferroelectric liquid crystal compounds.

Heretofore, in the above fields, optically active 2-butanol, 2-octanol, 2-methyl-1-butanol or an amino acid derivative has been used as a raw material for an optically active material. However, the obtained optically active materials are limited in characteristics so long as the above optically active materials are used.

In the field of ferroelectric liquid crystals, recently, attempts are being vigorously made to use, as a raw material, the following optically active alcohols in which a perfluoroalkyl group is substituted on their asymmetric carbon, for synthesizing ferroelectric liquid crystals (e.g., JP,A 64-3154, JP,A 1-316339, JP,A 1-316367, JP,A 1-316,372, JP,A 2-225,434 and JP,A 2-229,128).

(1) $CF_3C^*H(OH)CH_2COOC_2H_5$
(2) $CF_3C^*H(OH)CH_2CH_2OC_2H_5$
(3) $CF_3C^*H(OH)CH_2CH_2CH_2OC_2H_5$
(4) $CF_3C^*H(OH)CH_2CH_2CH_2CH_2OC_2H_5$
(5) $CF_3C^*H(OH)C_6H_{13}$
(6) $CF_3C^*H(OH)C_8H_{17}$
(7) $C_2F_5C^*H(OH)C_8H_{17}$

Ferroelectric liquid crystal compounds synthesized from the above alcohols all give high spontaneous polarization since a perfluoroalkyl group having high electro-negativity is substituted on the asymmetric carbon of each, and they give relatively fast response speeds.

It is also known that a liquid crystal compound synthesized from (5) $CF_3C^*H(OH)C_6H_{13}$, (6) $CF_3C^*H(OH)C_8H_{17}$ or (7) $C_2F_5C^*H(OH)C_8H_{17}$ is likely to give a liquid crystal having an anti-ferroelectric phase, and these alcohols are attracting attention as particularly characteristic alcohols.

Further, the present inventors made close studies on the process for the production of an optically active alcohol represented by $CF_3C^*H(OH)(CH_2)_mOC_nH_{2n+1}$ (m is an integer of 2 to 7 and n is an integer of 1 to 4), which has an alkoxy group as terminal group, and liquid crystal compounds synthesized therefrom, and as a result, it was found that the above alcohol gives very useful anti-ferroelectric liquid crystal compounds or ferroelectric-liquid crystal compounds (JP,A 5-65486 and JP,A 7-89207).

Anti-ferroelectric liquid crystal compound or a ferroelectric liquid crystal compound synthesized from an optically active alcohol containing an asymmetric carbon having a trifluoromethyl group substituted thereon shows very high spontaneous polarization. When the spontaneous polarization is high, the response speed is fast and hence, the high spontaneous polarization is advantageous in this respect.

With an increase in the spontaneous polarization, however, the mutual effects of an insulation layer and an alignment layer in an electrode cell on each other increase, and the deformation of hysteresis of voltage-optical transmission increases to an extraordinary extent. There is therefore liable to be a problem that no drive margin is permitted.

It is therefore desired that a liquid crystal compound which shows a small spontaneous polarization and at the same time, is free of problems on a response speed and a tilt angle, and development of a optically active secondary alcohol capable of showing such properties has been demanded.

Meanwhile, a optically active secondary alcohol can be produced by various methods.

In view of economic performance, however, it is not economical to use an optically active material as a raw material, since the optically active material is expensive.

First, an optically active alcohol may be also produced by asymmetric synthesis. For example, an optically active alcohol may be produced by preparing a corresponding ketone compound as a precursor and asymmetrically reducing it in the presence of an asymmetrically reduction catalyst. However, the asymmetrically reduction catalyst is very expensive. Further, a product having a high optical purity cannot be always obtained, and only one of an R-configuration compound or an S-configuration compound is obtained.

Secondly, a proper ester that is the precursor of an optically active compound, such as an acetate, may be asymmetrically hydrolyzed. An enzyme is used as an effective asymmetrically hydrolyzing agent. The asymmetric hydrolysis of an acetate with lipase has been proposed by Kitazume et al (T. Kitazume et al., J. Org. 52, 3211 (1987), JP,A 2-282,340).

According to the above method, an acetate represented by $CF_3CH(OCOCH_3)C_nH_{2n+1}$ is asymmetrically hydrolyzed in a phosphoric acid buffer solution in the presence of lipase MY. However, the capability of asymmetry recognition by lipase MY is greatly dependent upon the chemical structure of a compound to be hydrolyzed, and the optical purity of obtained hydrolysis products varies from 55 to 98 ee% depending upon chemical structures as shown in Table 1 in the literature by Kitazume et al.

The above results show that it is difficult to calculate whether or not an intended compound can be well asymmetrically hydrolyzed and that it is found only after a reaction whether or not an intended alcohol has a high optical purity.

Further, the serious problem is that the capability of asymmetry recognition is not at all exhibited when some substituent is on an asymmetric carbon.

For example, lipase MY exhibits the capability of asymmetry recognition in the asymmetric hydrolysis of $CF_3CH(OCOCH_3)(CH_2)_5OC_2H_5$. However, lipase MY does not show any asymmetry recognition for a secondary alcohol ester $CH_3CH(OCOCH_3)C_6H_{13}$ in which a methyl group is substituted on the asymmetric carbon.

In addition, a secondary alcohol can be also produced by a method in which a secondary racemic alcohol is asymmetrically trans-esterified in the presence of a proper enzyme and the optical resolution thereof is carried out.

One example is a reaction of asymmetric trans-esterification in an organic solvent in the presence of a lipase (derived from porcine pancreas) (A. M. Klibanov et al., J. Am. Chem. Soc. 1985, 106, 7072).

However, no lipase having high activity and high enantio-selectivity has been heretofore known.

The asymmetric hydrolysis using an enzyme and the optical resolution by asymmetric trans-esterification have an advantage in that both R-configuration and S-configuration compounds are easily obtained.

The following alcohols and processes are known as optically active alcohols containing an asymmetric carbon having a methyl group substituted thereon and having an alkoxy group as terminal group and processes for the production thereof.

Concerning 5-methoxypentane-2-ol ($CH_3C^*H(OH)(CH_2)_3OCH_3$), both R-configuration and S-configuration compounds are known. For example, the R-configuration compound is obtained from R-1,4-pentanediol as a raw material (25° C., specific rotation [α] for D ray=–12.5°) (JACS, 89, 73(1967)).

In the production of the above compound, R-1,4-pentanediol is used as a raw material, while it is a critical problem in the industry that the above raw material is very difficult to obtain. On the other hand, the S-configuration compound is synthesized from some carbamate as a raw material (25° C., specific rotation [α] for D ray=+12.6°), while the production thereof is not economical since it requires many production steps (U.S. Pat. No. 5,223,633).

Concerning 5-ethoxypentan-2-ol ($CH_3C^*H(OH)(CH_2)_3OC_2H_5$), an S-configuration compound is known (Biocatalysis, 3, 57(1990)). In the process for the production thereof, a corresponding ketone is asymmetrically reduced in the presence of an enzyme called *Thermoanaerobium brockii* alcohol dehydrogenase. In this process, a secondary alcohol having a high optical purity can be obtained, but an S-configuration compound alone can be produced.

Other optically active alcohols having chemical structures of $CH_3C^*H(OH)(CH_2)_3OC_3H_7$, $CH_3C^*H(OH)(CH_2)_4OC_nH_{2n+1}$ and $CH_3C^*H(OH)(CH_2)_5OC_nH_{2n+1}$ are not known yet.

The present invention has been made under the above circumstances, and it is an object of the present invention to provide a novel optically active secondary alcohol containing an asymmetric carbon having a methyl group substituted thereon and having an alkoxy group as terminal group, and an efficient process for the production thereof.

The present inventors have made diligent studies on the processes for the production of the above novel optically active secondary alcohols. As a result, it has been found that when the lipase derived from *Candida antarcia* microorganism is used as a catalyst in an asymmetric trans-esterification, the lipase exhibits very high reactivity per unit amount of the lipase and very high enantio-selectivity and that vinyl propionate is effective as an esterifying agent in the reaction.

That is, according to the present invention, there is provided a process for the production of an R-configuration or S-configuration optically active alcohol of the formula (1), $$CH_3C^*H(OH)(CH_2)_mOC_nH_{2n+1} \qquad (1)$$

wherein m is an integer of 3 to 5, n is an integer of 1 to 3 and C* is an asymmetric carbon, and the formula (2), which comprises carrying out the optical resolution of the racemic alcohol, $$CH_3C^*H(OH)(CH_2)_mOC_nH_{2n+1} \qquad (2)$$

wherein m is an integer of 3 to 5 and n is an integer of 1 to 3, into an R-configuration compound and an S-configuration compound by the asymmetric trans-esterification thereof in the presence of vinyl propionate as an esterifying agent and a lipase as a catalyst.

The present invention will be explained further in detail hereinafter.

The R-configuration or S-configuration optically active alcohol provided by the present invention has the above formula (1), in which a methyl group and a OH group are substituted on an asymmetric carbon and one terminal group is an alkoxy group. In the formula (1), m is an integer of 3 to 5, particularly preferably 3. n is an integer of 1 to 3, particularly preferably 2 or 3.

According to the present invention, the optically active alcohol of the above formula (1) can be produced by the optical resolution of the racemic alcohol of the above formula (2) into an R-configuration compound and an S-configuration compound by the asymmetric trans-esterification thereof. Specifically, the racemic alcohol of the above formula (2) is subjected to an asymmetric trans-esterification to obtain a reaction mixture containing an R-configuration compound of which the OH group is esterified, and the esterified R-configuration compound is isolated, or an S-configuration compound which is not esterified is isolated and the esterified R-configuration compound is hydrolyzed as required, whereby the optically active alcohol of the formula (1) is obtained. According to the present invention, therefore, each of the R-configuration optically active alcohol and the S-configuration optically active alcohol can be obtained.

In the present invention, the catalyst for the asymmetric trans-esterification is preferably a lipase derived from *Candida antarcia* microorganism. When vinyl propionate is used as an esterifying agent, the lipase derived from *Candida antarcia* microorganism gives very high reactivity per unit amount of the lipase and also very high enantio-selectivity (for example, an optical purity of 90% ee or more.).

The above lipase is preferably an immobilized enzyme obtained by immobilizing the lipase on a porous acrylic resin. Being commensurate with the reaction rate, the amount of the lipase used is properly determined depending upon a reaction time. In the present invention, the amount of the lipase is preferably 0.1 to 10 g per mole of the racemic alcohol as a raw material. The reaction temperature is preferably between 20° C. and 40° C. for attaining a sufficient reaction rate and enantio-selectivity.

In the present invention, an immobilized enzyme obtained by immobilizing the lipase to a porous acrylic resin produced and sold by Novo Nordisk A/S is preferred.

The R-configuration or S-configuration optically active alcohol (to be simply referred to as "optically active alcohol" hereinafter) of the formula (1) provided by the present invention is produced by a method in which a racemic alcohol as a precursor is prepared by a proper method and subjected to the optical resolution by asymmetric trans-esterification.

The lipase derived from *Candida antarcia*, suitably used in the present invention, has remarkably high reactivity as compared with lipase derived from porcine pancreas and Pseudomonas lipase which are known to have the optical resolution capability for a secondary alcohol, and produces a high reactivity even if used in a small amount. Being commensurate with the reaction rate, the amount of the lipase used is properly determined depending upon a reaction time. The amount of the lipase is generally 0.1 to 10 g per mole of the racemic alcohol as a precursor.

The racemic secondary alcohol as a raw material which is subjected to the asymmetric trans-esterification is easily produced, for example, by the following method. In the following reaction scheme, m and n are as defined in the formula (1).

(1) Method using alkyl dibromide as a starting material:

(a) $Br(CH_2)_mBr + NaOC_nH_{2n+1} \rightarrow Br(CH_2)_mOC_nH_{2n+1}$ (b) $(a) + Mg \rightarrow MgBr(CH_2)_mOC_nH_{2n+1}$ (c) $(b) + CH_3CHO \rightarrow CH_3CH(OH)(CH_2)_mOC_nH_{2n+1}$ The above reaction scheme will be briefly explained below.

(a) shows the production of an ether compound by a reaction between an alkyl dibromide and sodium alkyl oxide.

(b) shows the preparation of a Grignard reagent.

(c) shows the propagation reaction by a reaction between the Grignard reagent and acetaldehyde.

(2) Method using 3-acetyl-1-propanol as a starting material:

(a) $CH_3COCH_2CH_2CH_2OH + (C_nH_{2n+1}O)_2SO_2 \rightarrow CH_3COCH_2CH_2CH_2OC_nH_{2n+1}$ (b) $(a) + NaBH_4 \rightarrow CH_3CH(OH)CH_2CH_2CH_2OC_nH_{2n+1}$ The above reaction scheme will be briefly explained below.

(a) shows the etherification with dialkylsulfuric acid.

(b) shows the reduction of a carbonyl group.

(3) Method using ethyl β-ethoxypropionate as a raw material:

(a) $C_2H_5OCOCH_2CH_2OC_2H_5 + LiAlH_4 \rightarrow HOCH_2CH_2CH_2OC_2H_5$ (b) $(a) + PBr_3 \rightarrow BrCH_2CH_2CH_2OC_2H_5$ (c) $(b) + Mg + CH_3CHO \rightarrow CH_3CH(OH)(CH_2)_3OC_2H_5$ The above reaction scheme will be briefly explained below.

(a) shows the reduction of an ester portion.

(b) shows the bromination of an alcohol.

(c) shows the production of a racemic alcohol by a Grignard reaction.

As described above, the present invention provides the process for the production of the optically active alcohol of the formula (1).

The optically active alcohol of the formula (1) has a structural feature in that it contains an asymmetric carbon having a hydroxyl group and a methyl group substituted thereon and that it has an alkoxy group as terminal group.

The above optically active alcohol can be expected to have usefulness as raw material or an intermediate in various fields.

As far as the present inventors made researches, some of the above optically active alcohols are novel.

According to the present invention, there is provided an R-configuration optically active alcohol of the formula (1'), $$CH_3C^*H(OH)(CH_2)_mOC_nH_{2n+1} \qquad (1')$$

wherein m is an integer of 4 or 5, n is an integer of 1 to 3, and C* is an asymmetric carbon.

In the above optically active alcohol of the formula (1'), the alcohol in which n is 2 or 3 is preferable.

Further more, according to the present invention, there are provided an R-configuration optically active alcohols of 5-ethoxy-penta-2-ol and 5-propyloxy-penta-2-ol.

The above R-configuration optically active alcohol of the formula (1'), 5-ethoxy-penta-2-ol or 5-propyloxy-penta-2-ol which has an optical purity of 90% ee or more, is more preferred.

Studies by the present inventors have revealed that the optically active alcohol of the formula (1) is a valuable raw material for an anti-ferroelectric liquid crystal compound that has a small spontaneous polarization, and is novel and useful.

According to the present invention, there is provided an anti-ferroelectric liquid crystal compound of the following formula (3) from the optically active alcohol of the formula (1).

$$R-O-\bigcirc-\bigcirc-COO-\underset{X}{\bigcirc}-COO-\underset{CH_3}{C^*}H(CH_2)_mOC_nC_{2n+1} \qquad (3)$$

wherein R is a linear alkyl group, X is a hydrogen atom or a fluorine atom, m is an integer of 3 to 5, n is an integer of 1 to 3 and C* is an asymmetric carbon.

A liquid crystal display device has been so far applied to various small-sized display devices for reasons of its low-voltage operability, low power consumption and thin display capability. With recent broadening of application and use of liquid crystal display devices to/in the fields of an information and office automation-related machine and equipment or television, there are rapidly growing demands for high-performance, large-sized liquid crystal display devices having higher display capacity and higher display quality over existing CRT display devices.

However, so long as a nematic liquid crystal available at present is used, even an active matrix driven liquid crystal display device (TFT) used in a liquid crystal television set finds it not easy to increase its size and decrease its production cost due to its complicated production process and low yield. In a simple matrix-driven STN liquid crystal display device (STN), large display capacity driving is not necessarily easy and its response time is limited, so that video frame display is therefore difficult. In practical case, a nematic liquid crystal display device does not satisfy the above demands for high-performance, large-sized liquid crystal display devices.

Further, with regard to a display quality, both TFT and STN display devices using a nematic liquid crystal have a problem in the narrowness of their viewing angle. Various methods of improvements have been proposed, but it is difficult to find an essential solution thereof so long as a nematic liquid crystal is used.

Under the circumstances, it is a liquid crystal display using a ferroelectric liquid crystal that is attracting attention as a liquid crystal display device which performs at a high-response with a wide viewing angle. A surface stabilized ferroelectric liquid crystal (SSFLC) device disclosed by Clark and Lagerwall attracts attention in that it has a fast response speed and a wide viewing angle which have not been attained in the past. Its switching characteristics have been studied in detail, and a large number of ferroelectric liquid crystal compounds have been synthesized for optimizing various physical property constants.

Since, however, it has problems that its threshold characteristic is insufficient and that its layer has a chevron structure, its liquid crystal alignment requires some particular devising or designing for attaining a high contrast ratio in practical use. Further, the alignment control is difficult so that it is not easy to accomplish, with well reproducibility, the bistability which is one of the greatest characteristics of SSFLC. Further, another problem is that the liquid crystal alignment destroyed by mechanical shock is difficult to restore. It is therefore required to overcome these problems for its practical use.

As described above, much efforts have been being made to develop a new mode for an increase in the size of a liquid crystal display and the higher resolution thereof, while devices having completely different switching mechanisms are also being concurrently developed in these situations.

Switching among tristable states of a liquid crystal substance having an anti-ferroelectric phase (to be referred to as "anti-ferroelectric liquid crystal" hereinafter) is also one of these new switching mechanisms (Japanese Journal of Applied Physics, Vol. 27, pp. L729, 1988).

An anti-ferroelectric liquid crystal device has three stable states, i.e., two uniform states (Ur, Ul) observed in a ferroelectric liquid crystal device and a third state. Chandani et al report that the above third state is an anti-ferroelectric phase (Japanese Journal of Applied Physics, vol.28, pp. L1261, 1989, Japanese Journal of Applied Physics, vol.28, pp. L1265, 1989). The above switching among tristable states is the first characteristic of an anti-ferroelectric liquid crystal device.

The second characteristic of the anti-ferroelectric liquid crystal device is that a sharp threshold is present relative to an applied voltage. Further, it has a memory effect, which is the third characteristic of the anti-ferroelectric liquid crystal device. By utilizing these excellent characteristics, a liquid crystal display device having a fast response and a good contrast can be achieved.

The anti-ferroelectric liquid crystal has another great characteristic in that its layer structure easily switches when an electric field is applied (Japanese Journal of Applied Physics, Vol. 28, pp. L119, 1989, Japanese Journal of Applied Physics, vol. 29, pp. L111, 1990).

On the basis thereof, a liquid crystal display device almost free of defects and capable of self-restoring alignment can be produced, and a liquid crystal display device having an excellent contrast can be achieved.

As anti-ferroelectric liquid crystal compounds, there are known those which are disclosed in JP,A 1-213390, JP,A 1-316339, JP,A 1-316367, JP,A 1-316,372, JP,A 2-28128 and "Liquid Crystals" Vol. 6, pp. 167 (1989).

The number of the anti-ferroelectric liquid crystal compounds that have been found so far is not large as compared with ferroelectric liquid crystal compounds, while the number thereof is gradually increasing with an advance in their studies.

As described already, a ferroelectric liquid crystal compound, an anti-ferroelectric liquid crystal compound and a ferroelectric liquid crystal compound are provided from an optically active alcohol containing an asymmetric carbon having a perfluoroalkyl group substituted thereon.

However, all of the above liquid crystal compounds have high spontaneous polarization and have problems in practical use. That is, the anti-ferroelectric liquid crystal compound shows a remarkable deformation of hysteresis as to voltage-optical transmission and almost no driving margin is permitted, and the ferroelectric liquid crystal compound can no longer be driven at a low voltage.

It has been therefore desired to develop an anti-ferroelectric liquid crystal or a ferroelectric liquid crystal that shows a decreased spontaneous polarization.

According to the present invention, it has been found that a biphenyl-ester-containing liquid crystal compound obtained from the optically active alcohol, represented by the above formula (1), containing an asymmetric carbon having a methyl group substituted thereon and having an alkoxy group as terminal group is an anti-ferroelectric liquid crystal compound which shows a remarkably decreased spontaneous polarization.

That is, the anti-ferroelectric liquid crystal compound of the above formula (3), provided by the present invention, can be easily obtained from the optically active alcohol of the above formula (1), and it is a liquid crystal compound which shows a decreased spontaneous polarization and has remarkable practical usefulness.

In the formula (3), the linear alkyl group represented by R preferably has 8 to 10 carbon atoms from standpoints of the stable exhibition of an anti-ferroelectric phase and the temperature range of the anti-ferroelectric phase.

Further, when m is 3 and n is 2 or 3 in the formula (3), preferably, the anti-ferroelectric liquid crystal compound stably exhibits an anti-ferroelectric phase.

The anti-ferroelectric liquid crystal compound of the formula (3) can be produced by reactions known per se except for the use of the alcohol of the formula (1) as an optically active alcohol. One embodiment of the production process thereof will be explained below.

(a) $AcO\text{-}Ph(X)\text{-}COOH + SOCl_2 \rightarrow AcO\text{-}Ph(X)\text{-}COCl$ (b) $(a) + CH_3C^*H(OH)(CH_2)_m OC_n H_{2n+1} \rightarrow AcO\text{-}Ph(X)\text{-}COO\text{-}C^*H(CH_3)(CH_2)_m OC_n H_{2n+1}$ (c) $(b) + Ph\text{-}CH_2NH_2 \rightarrow HO\text{-}Ph(X)\text{-}COO\text{-}C^*H(CH_3)(CH_2)_m OC_n H_{2n+1}$ (d) $R\text{-}O\text{-}Ph\text{-}Ph\text{-}COOH + SOCl_2 \rightarrow R\text{-}O\text{-}Ph\text{-}Ph\text{-}COCl$ (e) (c)+(d)→Liquid crystal compound as an end product.

In the above reaction scheme, AcO is an acetyl group, -Ph- is a 1,4-phenylene group, -Ph(X)- is a 1,4-phenylene group in which a fluorine atom may be substituted on the 3-position of the benzene ring, Ph- is a phenyl group, C* is an asymmetric carbon, and m and n are as defined in the formula (3).

The above production process will be briefly explained below.

(a) shows the chlorination of p-acetoxybenzoic acid with thionyl chloride.

(b) shows the formation of an ester by a reaction between the chloride (a) and the optically active alcohol of the formula (1).

(c) shows the deacetylation of the ester (b).

(d) shows the chlorination of 4'-alkyloxybiphenyl-4-carboxylic acid.

(e) shows the production of a liquid crystal compound as an end product by a reaction between the phenol (c) and the chloride (d).

According to the present invention, there is provided an economical and simple process for production of an optically active secondary alcohol containing an asymmetric carbon having a methyl group substituted thereon and having an alkoxy group as terminal group, and a novel R-configuration optically active alcohols.

According to the present invention, further, there is provided a novel anti-ferroelectric liquid crystal compound produced from the above novel optically active alcohol. The anti-ferroelectric liquid crystal compound is useful as a liquid crystal material, which has a remarkably low spontaneous polarization and excellent utility.

EXAMPLES

The present invention will be explained further in detail with reference to Examples hereinafter, while the present invention shall not be limited to these Examples.

Example 1

[Preparation of R-(−)-5-ethoxy-pentan-2-ol, the formula (1): m=3, n=2 (E1)]

(1) Synthesis of 3-ethoxy-1-propanol

A reactor equipped with a reflux condenser, a stirrer and a dropping funnel was charged with 52.7 g of lithium aluminium hydride and 1,400 ml of ether. While the mixture was sitrred, a solution of 305 g of 3-ethoxypropionic acid ethyl ester in ether was dropwise added at room temperature. Gas chromatography was used to confirm the consumption of the raw materials, and then, a mixture of water and THF (tetrahydrofuran) was slowly dropwise added with cooling, to carry out the decomposition of excessive hydride and hydrolysis. A formed solid was filtration and dried over anhydrous sodium sulfate.

The ether was removed and then a remainder was distilled under vacuum to give an end product (yield 80%, purity by gas chromatography 99%, boiling point 99° C./94 mmHg).

(2) Synthesis of 3-ethoxy-1-bromopropane

A reactor equipped with a stirrer, a reflux condenser and a dropping funnel was charged with 353 g of the 3-ethoxy-1-propanol obtained in (1), and 308 g of phosphorus tribromide was dropwise added with cooling. After the dropwise addition, gas chromatography was used to confirm the consumption of the raw materials, and then, the reaction mixture was extracted with dichloromethane. Then, the extract was dried over anhydrous sodium sulfate. After the removal of the solvent, the residue was distilledunder vacuum to give an end product (yield 61%, purity by gas chromatography 95%, boiling point 84/91 mmHg).

(3) Preparation of 5-ethoxy-pentan-2-ol (recemic compound)

4.2 Gram of metal Mg was placed in a round-bottom flask, and atmosphere inside the flask was purged with nitrogen. Then, 50 ml of dry THF was added, and a solution of 27.2 g of the 3-ethoxy-1-bromopropane obtained in (2) in 50 ml of dry THF was dropwise added at room temperature. The mixture was allowed to react for aging for 1 hour.

Separately, 0.1 g of p-toluenesulfonic acid was placed in other container, and while it was heated at 50 to 70° C., 11.4 g of p-acetoaldehyde was dropwise added to generate acetoaldehyde. The acetoaldehyde was blown into the reactor over the period of 2 hours. The reaction mixture was treated with 1N hydrochloric acid and extracted with ether. The resultant ether solution was washed with water and then dried over anhydrous sodium sulfate. The ether was distilled off, and the remainder was purified by vacuum distillation and column chromatography (yield 52%).

(4) Preparation of R-(−)-5-ethoxy-pentane-2-propionate 2.7 Grams of vinyl propionate and 40 mg of lipase (Novozym 435, supplied by Novo Nordisk A/S) were added to 4.9 g of the racemic secondary alcohol obtained in (3), and the mixture was stirred at room temperature for 24 hours. After the completion of the reaction, the lipase was filtered off, the remainder was washed with hexane, and remaining raw materials, etc., were distilled off. The remainder was purified by silica gel column chromatography to give 2.3 g (yield 33%) of an oil end compound and 2.2 g (yield 45%) of R-(+)-5-ethoxy-pentane-2-propionate.

(5) Preparation of R-(−)-5-ethoxy-pentan-2-ol 2.2 Grams of the R-(−)-5-ethoxy-pentan-2-propionate obtained in (4) was added to 20 ml of a solution of 2.2 g of potassium hydroxide in water-methanol (1:3), and the mixture was stirred at room temperature for 1 hour. After the completion of the reaction, the reaction mixture was extracted with ether, and an organic layer was washed with water and a saturated sodium chloride aqueous solution, and dried over anhydrous sodium sulfate. The anhydrous sodium sulfate was filtered off and then, the ether was distilled off to give 1.1 g of an end product (yield 70%).

Table 1 shows NMR spectral data of the end product (E1) obtained above.

Further, the R-(−)-5-ethoxy-pentan-2-ol was determined for an optical purity.

The R-(−)-5-ethoxy-pentan-2-ol was converted to an acetate with pyridine/anhydrous acetic acid.

The so-obtained acetate was analyzed by gas chromatograph used for the analysis of optically active compounds (CP Cyclodex β 236M), and the purity was determined on the basis of the ratio of peak areas of two enantiomers.

Further, the acetate was measured for a specific rotation while using chloroform as a solvent.

Table 2 shows the results.

Example 2

[Preparation of R-(−)-5-propyloxy-pentan-2-ol, the formula (1): m=3, n=3 (E2)]

(1) Preparation of 3-acetyl-1-propyloxy-propane

50 Grams of 3-acetyl-1-propanol was placed in a round-bottom flask, and 98 g of di-n-propylsulfuric acid and 90 ml of a 40% potassium hydroxide aqueous solution were concurrently dropwise added. The reaction temperature was maintained at 70 to 80° C. by adjusting the dropping amount. After the completion of the reaction, the reaction mixture was extracted with ether, and an ether layer was washed with water and then dried over anhydrous sodium sulfate. The ether was distilled off, and the remainder was vacuum-distilled for isolation and purification, to give 34.8 g of an end product (85° C./20 mmHg; yield 50%).

(2) Preparation of 5-propyloxy-pentan-2-ol (racemic compound)

To 34.8 g of the 3-acetyl-1-propyloxy-propane obtained in (1) was added 50 ml of methanol, and a solution of 44.4 g of $NaBH_4$ in 8% sodium hydroxide was dropwise added at room temperature. After the reaction, the methanol was distilled off, 200 ml of water was added, and the mixture was extracted with ether. An organic layer was washed with water and dried over anhydrous sodium sulfate. The anhydrous sodium sulfate was filtered off, then, the ether was distilled off, and the remainder was distilled under vacuum for isolation and purification (104° C./20 mmHg; yield 40%).

(3) Preparation of R-(−)-propyloxy-pentan-2-ol

R-(−)-propyloxy-pentan-2-ol and S-(+)-propyloxy-pentan-2-ol were prepared from the racemic secondary alcohol obtained in the above (2) in the same manner as in Example 1 (4) and (5).

Table 1 shows NMR spectral data of the obtained R-configuration optically active alcohol. Further, the R-configuration compound was measured for an optical purity and a specific rotation in the same manner as in Example 1. Table 2 shows the results.

Example 3

[Preparation of R-(−)-6-methoxy-hexan-2-ol, the formula (1): m=4, n=1 (E3)]

(1) Preparation of 3-methoxy-1-bromobutane

260 Grams of a solution of 20% of sodium methoxide in methanol was dropwise added to 190 g of 1,4-dibromobutane at a reaction temperature of 40° C. or lower. After the completion of the dropwise addition, the mixture was continuously stirred for 1 hour, and then, the methanol was distilled off under reduced pressure. The resultant crude product was washed with 1% hydrochloric acid and then washed with water. The washed crude product was purified by distillation (70° C./30 mmHg; yield 40%).

(2) Preparation of 6-methoxy-hexan-2-ol (recemic compound)

A Grignard reaction was carried out in the same manner as in Example 1 (3) to give an end product. The obtained crude product was purified by silica gel column chromatography (yield 30%).

(3) Preparation of R-(−)-6-methoxy-hexane-2-ol

An R-configuration compound as an end product and an S-configuration optically active alcohol were obtained from the racemic compound obtained in the above (2), in the same manner as in Example 1 (4) and (5).

Table 1 shows NMR spectral data of the obtained R-configuration optically active alcohol. Further, the R-configuration compound was measured for an optical purity and a specific rotation in the same manner as in Example 1. Table 2 shows the results.

Example 4

[Preparation of R-(−)-7-ethoxy-heptan-2-ol, the general formula (1); m=5, n=2 (E4)]

An R-configuration end product and an S-configuration optically active alcohol were obtained in the same manner as in Example 3 except that the 1,3-dibromobutane was replaced with 1,5-dibromopentane and that the sodium methoxide was replaced with sodium ethoxide.

Table 1 shows NMR spectral data of the obtained R-configuration optically active alcohol. Further, the R-configuration compound was measured for an optical purity and a specific rotation in the same manner as in Example 1. Table 2 shows the results.

Example 5

[Preparation of R-(−)-5-methoxy-pentan-2-ol, the general formula (1); m=3, n=1 (E5)]

An R-configuration end product and an S-configuration optically active alcohol were obtained in the same manner as in Example 1 except that the di-n-propyl sulfate was replaced with dimethyl sulfate.

Table 1 shows NMR spectral data of the obtained R-configuration optically active alcohol, and Table 2 shows the optical purity and specific rotation thereof.

TABLE 1

| Ex. No. & Symbol | Compound and proton number | Chemical Shift (ppm) | | | | | |
|---|---|---|---|---|---|---|---|
| | | 1 | 2 | 3 | 4 | 5 | 6 |
| Ex. 1 (E1) | $CH_3C^*H(OH)CH_2CH_2CH_2OCH_2CH_3$<br>1  2  3  4  5  6 | 1.2 | 3.8 | 2.7 | 1.6 | 3.6 | 3.6 |
| Ex. 2 (E2) | $CH_3C^*H(OH)CH_2CH_2CH_2OCH_2CH_2CH_3$<br>1  2  3  4  5  6 | 1.2 | 3.8 | 2.8 | 1.6 | 3.4 | 3.4 |
| Ex. 3 (E3) | $CH_3C^*H(OH)CH_2CH_2CH_2CH_2OCH_3$<br>1  2  3  4  5  6 | 1.2 | 3.8 | 1.7 | 1.6 | 3.4 | 3.4 |
| Ex. 4 (E4) | $CH_3C^*H(OH)CH_2CH_2CH_2CH_2CH_2OC_2H_5$<br>1  2  3  4  5 | 1.2 | 3.8 | 1.7 | 1.6 | 3.4 | |
| Ex. 5 (E5) | $CH_3C^*H(OH)CH_2CH_2CH_2OCH_3$<br>1  2  3  4  5  6 | 1.2 | 3.8 | 2.4 | 1.5 | 3.4 | 3.4 |

Ex. = Example

TABLE 2

| Ex. No. | Chemical structure | Optical purity (% ee) | Specific rotation (°) |
|---|---|---|---|
| 1 (E1) | $CH_3C^*H(OH)(CH_2)_3OC_2H_5$ | 92.7 | −18.8 |
| 2 (E2) | $CH_3C^*H(OH)(CH_2)_3OC_3H_7$ | 96.7 | −18.6 |
| 3 (E3) | $CH_3C^*H(OH)(CH_2)_4OCH_3$ | 96.2 | −9.96 |
| 4 (E4) | $CH_3C^*H(OH)(CH_2)_5OC_2H_5$ | 97.1 | −7.6 |
| 5 (E5) | $CH_3C^*H(OH)(CH_2)_3OCH_3$ | 96.6 | −18.3 |

Ex. = Example

Example 6

[Preparation of R-(−)-4-(1-methyl-4-ethoxybutyloxycarbonyl)phenyl=4-(4'-n-nonyloxybiphenyl)carboxylate; the formula (1): $R=C_9H_{19}$, X=H, m=3, n=2 (L1)]

(1) Preparation of 4-(4'-n-nonyloxybiphenyl)carboxylic acid

10 Grams of 4-(4'-hydroxybiphenyl)carboxylic acid and 14.0 g of n-nonyl bromide were added to a mixture containing 1,500 ml of ethanol and 200 ml of water, and the resultant mixture was allowed to react under reflux for 10 hours. Further, 500 ml of water was added, and the mixture was stirred for 3 hours. After the completion of the reaction, concentrated hydrochloric acid was added to acidify the reaction product, 500 ml of the solvent was distilled off, and the remainder was cooled to room temperature to give a white solid.

The white solid was fully washed with water and recrystallized from chloroform to give 14.0 g of an end product in the form of a white crystal.

(2) Preparation of 4-acetoxybenzoic acid

6 Grams of 4-hydroxybenzoic acid and 8.2 g of anhydrous acetic acid were placed in a two-necked flask and mixed. While the mixture was cooled with water, 5 drops of sulfuric acid was added. After termination of heat generation, the mixture was heated at 80° C. for 30 minutes. Then, the reaction mixture was poured into cold water, and a precipitated crystal was filtered.

The crystal was vacuum-dried and then used in the following step. The yield thereof was 4.8 g.

(3) Preparation of R-(−)-4-acetoxy-1-(1-methyl-4-ethoxybutyloxycarbonyl)benzene 2.3 Grams of 4-acetoxybenzoic acid was added to 10 ml of thionyl chloride, and the mixture was allowed to react under reflux for 5 hours. Then, excessive thionyl chloride was distilled off, and then a mixture containing 1 ml of pyridine, 4 ml of dry ether and 2.0 g of R-(−)-5-ethoxypentan-2-ol obtained in Example 1 was dropwise added. After the dropwise addition, the mixture was stirred at room temperature over 1 day and night, diluted with 200 ml of ether, and an organic layer was washed with diluted hydrochloric acid, with a 1N sodium hydroxide aqueous solution and with water in this order, and then dried over magnesium sulfate.

The solvent was distilled off, and the resultant crude product was purified by silica gel column chromatography using hexane/ethyl acetate as solvents to give 1.6 g of an end product.

(4) Preparation of R-(−)-4-hydroxy-1-(1-methyl-4-ethoxybutyloxycarbonyl)benzene 1.0 Gram of the compound obtained in the above (3) was dissolved in 30 ml of ethanol, and 3 g of benzylamine was dropwise added. Further, the mixture was stirred at room temperature over 1 day and night, then diluted with 300 ml of ether, washed with diluted hydrochloric acid and with water in this order, and dried over magnesium sulfate.

The solvent was distilled off, and silica gel column chromatography was used to isolate and purify the resultant product to give 0.30 g of an end product.

(5) Preparation of 4-(4'-n-nonyloxybiphenyl)carboxylic acid chloride

A large excess of thionyl chloride was added to 10 g of the 4-(4'-n-nonyloxybiphenyl)carboxylic acid prepared in (1), and the mixture was refluxed for 5 hours. A large excess of the thionyl chloride was distilled off to give a crude end compound.

(6) Preparation of R-(−)-4-(1-methyl-4-ethoxybutyloxycarbonyl)phenyl=4-(4'-n-octyloxybiphenyl) carboxylate 0.7 Gram of the crude 4-(4'-n-nonyloxybiphenyl)carboxylic acid chloride obtained in (5) and 0.7 g of the phenol derivative obtained in (4) were dissolved in 25 ml of toluene, and after addition of 4 ml of pyridine, and the mixture was stirred over 1 day and night. The reaction mixture was diluted with 150 ml of dichloromethane and washed with a 1N hydrochloric acid aqueous solution, with a 1N sodium hydroxide aqueous solution and with water, and dried over anhydrous sodium sulfate, and the solvent was distilled off.

The resultant crude product was purified by silica gel column chromatography to give 0.3 g of an intended liquid crystal compound (L1).

Table 3 shows $^1$H-NMR data of the obtained liquid crystal compound (L1), and its chemical formula is shown by L1.

Phases thereof were identified by texture observation and measurement with a DSC (differential scanning calorimeter). Table 4 shows the results.

A liquid crystal cell (cell thickness 2 $\mu$m) having rubbed thin polyimide film and ITO electrode was filled with the above compound in an isotropic state. The cell was gradually cooled at a rate of 1.0° C./minute to align the liquid crystals. The compound was measured for a polarization inverting voltage by applying a triangular wave voltage of ±40V and 0.5 Hz to the above cell at a temperature which was 10° C. lower than a transition temperature to an antiferroelectric phase from isotropic, smectic A or smectic C* phase, to determine a spontaneous polarization. Table 4 shows the obtained spontaneous polarization.

Examples 7–11 and Comparative Examples 1 and 2

The following compounds were synthesized according to the method described in Example 6.

Table 3 shows $^1$H-NMR data of the obtained compounds (L2 to L6), and their chemical formulae are shown by L2 to L6.

Further, these compounds were measured for phase sequences and spontaneous polarization. Table 4 shows the results.

Example 7

R-(−)-3-fluoro-4-(1-methyl-4-ethoxybutyloxycarbonyl)phenyl=4-(4'-n-decyloxybiphenyl)carboxylate (the formula (1): R=$C_{10}H_{21}$, X=F, m=3, n=2 (L2))

Example 8

R-(−)-3-fluoro-4-(1-methyl-4-propyloxybutyloxycarbonyl)phenyl=4-(4'-n-octyloxybiphenyl)carboxylate (the formula (1): R=$C_8H_{17}$, X=F, m=3, n=3 (L3))

Example 9

R-(−)-3-fluoro-4-(1-methyl-5-methoxypentyloxycarbonyl)phenyl=4-(4'-n-nonyloxybiphenyl)carboxylate (the formula (1): R=$C_9H_{19}$, X=F, m=4, n=1 (L4))

Example 10

R-(−)-4-(1-methyl-6-ethoxyhexylcarbonyl)phenyl=4-(4'-n-octyloxybiphenyl)carboxylate (the formula (1): R=$C_8H_{17}$, X=H, m=5, n=2 (L5))

Example 11

R-(−)-3-fluoro-4-(1-methyl-6-ethoxyhexyloxycarbonyl)phenyl=4-(4'-n-octyloxybiphenyl)carboxylate (the formula (1): R=$C_8H_{17}$, X=F, m=5, n=2 (L6))

Comparative Example 1

R-(−)-3-fluoro-4-(1-methyl-4-methoxybutyloxycarbonyl)phenyl=4-(4'-n-decyloxybiphenyl)carboxylate (the formula (1): R=$C_{10}H_{21}$, X=F, m=3, n=1 (L7))

Comparative Example 2

R-(+)-3-fluoro-4-(1-trifluoromethyl-6-ethoxyhexyloxycarbonyl)phenyl=4-(4'-n-octyloxybiphenyl) carboxylate (the formula (1): R=$C_8H_{17}$, X=F, m=5, n=2, the substituent on asymmetric carbon was changed from —$CH_3$ to —$CF_3$ (L8))

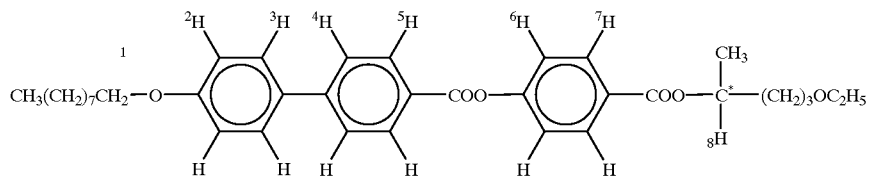
(L1)
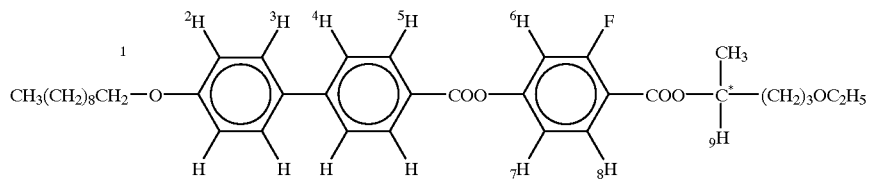
(L2)
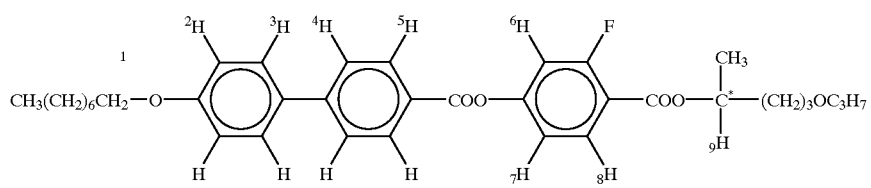
(L3)
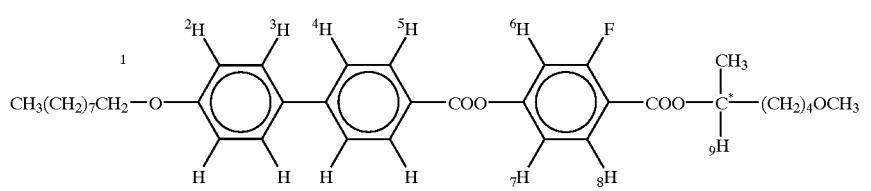
(L4)
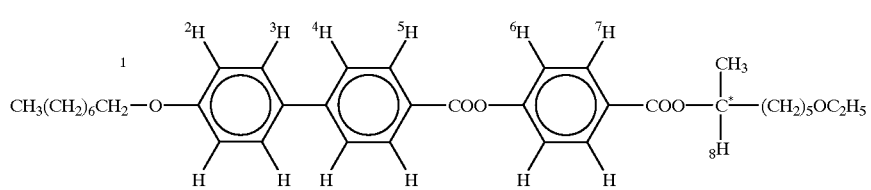
(L5)
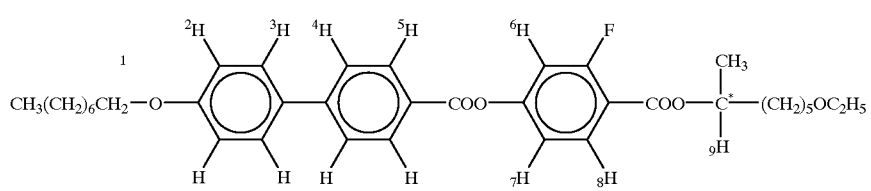
(L6)
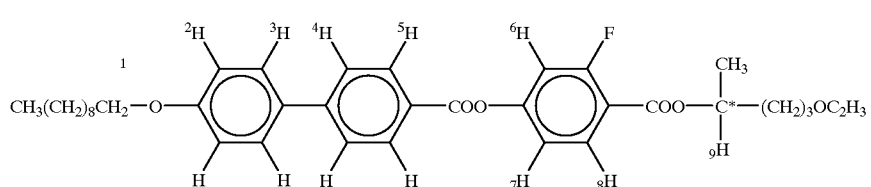
(L7)
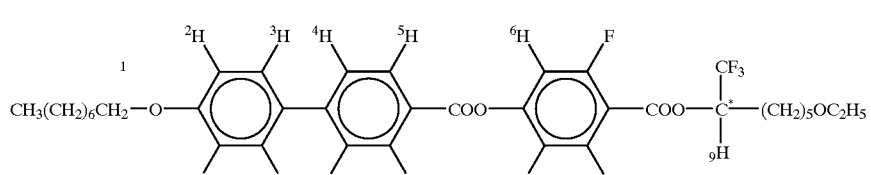
(L8)

TABLE 3

| | | Chemical shift | | | | | | | | |
|---|---|---|---|---|---|---|---|---|---|---|
| | | 1 | 2 | 3 | 4 | 5 | 6 | 7 | 8 | 9 |
| Ex. 6 | (L1) | 4.0 | 7.0 | 7.6 | 7.7 | 8.3 | 7.3 | 8.2 | 5.2 | |
| Ex. 7 | (L2) | 4.0 | 7.0 | 7.6 | 7.7 | 8.2 | 7.2 | 7.2 | 8.0 | 5.2 |
| Ex. 8 | (L3) | 4.0 | 7.0 | 7.6 | 7.7 | 8.2 | 7.2 | 7.2 | 8.0 | 5.2 |
| Ex. 9 | (L4) | 4.0 | 7.0 | 7.6 | 7.7 | 8.2 | 7.2 | 7.2 | 8.0 | 5.2 |
| Ex. 10 | (L5) | 4.0 | 7.0 | 7.6 | 7.7 | 8.2 | 7.2 | 8.2 | 5.2 | |
| Ex. 11 | (L6) | 4.0 | 7.0 | 7.6 | 7.7 | 8.2 | 7.2 | 7.2 | 8.0 | 5.2 |
| CEx. 1 | (L7) | 4.0 | 7.0 | 7.6 | 7.7 | 8.2 | 7.2 | 7.2 | 8.0 | 5.2 |
| CEx. 2 | (L8) | 4.0 | 7.0 | 7.6 | 7.7 | 8.2 | 7.2 | 7.2 | 8.0 | 5.2 |

Ex. = Example, CEx. = Compartive Example

TABLE 4

| | | Phase sequence | Spontaneous polarization |
|---|---|---|---|
| Ex. 6 | (L1) | Cr(61)SCA*(115)SA(133)I | 50 |
| Ex. 7 | (L2) | Cr(<-10)SCA*(112)SCγ*(113)SA(124)I | 42 |
| Ex. 8 | (L3) | Cr(48)SCA*(112)SC*(116)SA(133)I | 24 |
| Ex. 9 | (L4) | Cr(54)SCA*(103)SCγ*(105)SA(121)I | 38 |
| Ex. 10 | (L5) | Cr(<-10)SCA*(107)SA(130)I | 50 |
| Ex. 11 | (L6) | Cr(34)SCA*(107)SA(121)I | 34 |
| CEx. 1 | (L7) | Cr(<-10)SC*(110)SA(123)I | — |
| CEx. 2 | (L8) | Cr(40)SCA*(90)I | 165 |

In the phase sequences in Table 4, parenthesized values show transition temperatures (° C.), Cr is a crystal phase, SCA* is an anti-ferroelectric phase, SC* is a ferroelectric phase, SCγ* is a ferroelectric phase, and I is an isotropic phase. The unit of the spontaneous polarization is nC/cm².

Comparative Example 3

A reaction was carried out in the same manner as in Example 1 (4) except that 2.67 grams of divinyl adipate was used in place of 2.7 g of vinyl propionate.

After the completion of the reaction, the lipase was filtered off and the remainder was washed with hexane. The reaction rate and optical purity were calculated by analyzing the remainder by capillary column gas chromatography. Since the gas chromatograph of an FID detector was used, the integral ratio of alcohols to carboxylic esters can be made approximate to the weight ratio of these and a molar ratio can be calculated therefrom. The reaction rate and optical purity were obtained from the molar ratio. The conditions of gas chromatography are as follows.

| Capillary column | |
|---|---|
| Filler | CP-Cyclodextrin-B-236-M-19 |
| Length of column | 0.25 φ × 25 m (GL Science) |
| Carrier | Nitrogen |
| Flow rate | 1.0 ml/min (split ration: 39:1) |
| Detector | FID |
| Column temperature | 100° C. (fixed) |
| Injection temperture | 200° C. |
| Sample concentration 2% | |
| Amount of charge | 0.4 μm |

The adipic ester obtained by the reaction has a high boiling point and cannot be analyzed by gas chromatography. Then, using the vinyl propionate of HOCH(CH$_3$)C$_3$H$_6$OC$_2$H$_5$ which is a racemic compound as an internal reference, the consumption of a racemic alcohol was calculated to obtain the reaction rate. Unreacted alcohol was converted into acetate and the optical purity of the racemic compound was calculated from the optical purity and reaction rate of the acetate. As a result, the reaction rate was 29.7% and the optical purity of the racemic compound was 30.8% ee.

Comparative Example 4

A reaction was carried out and the reaction product was treated in the same manner as in Example 1 (4) except that 6.1 grams of vinyl laurate was used in place of 2.7 g of vinyl propionate. The obtained remainder was analyzed by gas chromatography as in Comparative Example 3. As a result, the reaction rate was 24.7% and the optical purity of the racemic compound was 16.1% ee.

Comparative Example 5

A reaction was carried out and the reaction product was treated in the same manner as in Example 1 (4) except that 40 mg of lipase derived from Pseudomonas was used in place of 40 mg of lipase (Novogym 435). The obtained remainder was analyzed by gas chromatography as in Comparative Example 3.

The reaction rate and optical purity were obtained by gas chromatography making a simple manner of area ratio. As a result, the reaction rate after 24 hours was 34.5% and the optical purity of a racemic propionic ester was 80.1% ee.

What is claimed is:

1. A process for the production of an optically active alcohol having an optical purity of 90% ee or more from a racemic alcohol of the formula (2), which comprises carrying out the optical resolution of the racemic alcohol, $$CH_3CH(OH)(CH_2)_mOC_nH_{2n+1} \qquad (2)$$

wherein m is an integer of 3 to 5 and n is an integer of 1 to 3, into an R-configuration compound and an S-configuration compound by the asymmetric trans-esterification thereof in the presence of vinyl propionate as an esterifying agent and a lipase as a catalyst, wherein the lipase catalyst is derived from *Candida antarcia* and is used in an amount of 0.1 to 10 g per mole of the racemic alcohol and the trans-esterification is carried out at a temperature between 20° C. and 40° C.

2. The process of claim 1, wherein the racemic alcohol has the formula (2) in which m is the integer 3 and n is an integer of 2 to 3.

3. The process of claim 1, wherein the racemic alcohol has the formula (2) in which m is the integer 4 and n is an integer of 2 to 3.

4. The process of claim 1, wherein m is the integer 5 and n is an integer of 2 to 3.

5. The process of claim 1, wherein the lipase is an immobilized enzyme prepared by immobilizing the lipase to a porous acrylic resin.

* * * * *

UNITED STATES PATENT AND TRADEMARK OFFICE
CERTIFICATE OF CORRECTION

PATENT NO. : 6,103,517
DATED : August 15, 2000
INVENTOR(S) : Takakiyo MINE, Tomoyuki YUI, Masahiro JOHNO It is certified that error appears in the above-indentified patent and that said Letters Patent is hereby corrected as shown below:

On the title page, item [30],

Delete "2-240519" and substitute therefore --8-240519--; and

Delete "8-284749" and substitute therefore --8-254749--.

Signed and Sealed this

Twenty-fourth Day of April, 2001

Attest:

NICHOLAS P. GODICI

Attesting Officer

Acting Director of the United States Patent and Trademark Office